US012806368B2

(12) United States Patent
Davis et al.

(10) Patent No.: US 12,806,368 B2
(45) Date of Patent: Nov. 24, 2026

(54) CATHETER PATENCY DEVICE

(71) Applicant: Bard Access Systems, Inc., Salt Lake City, UT (US)

(72) Inventors: Michael Davis, West Jordan, UT (US); Gidon Ofek, Millcreek, UT (US); Edward David Bell, Kearns, UT (US); Samuel Joseph Akins, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 490 days.

(21) Appl. No.: 17/065,941

(22) Filed: Oct. 8, 2020

(65) Prior Publication Data

US 2021/0128869 A1 May 6, 2021

Related U.S. Application Data

(60) Provisional application No. 62/928,231, filed on Oct. 30, 2019.

(51) Int. Cl.
*A61M 25/00* (2006.01)
*A61M 1/00* (2006.01)

(52) U.S. Cl.
CPC .......... *A61M 25/0017* (2013.01); *A61M 1/74* (2021.05); *A61M 1/77* (2021.05);
(Continued)

(58) Field of Classification Search
CPC ...... A61M 1/77; A61M 1/85; A61M 25/0017; A61M 1/74; A61M 1/84; A61M 2202/04;
(Continued)

(56) References Cited

U.S. PATENT DOCUMENTS

| | | | |
|---|---|---|---|
| 3,433,226 A | 3/1969 | Boyd | |
| 3,812,841 A | 5/1974 | Isaacson | |

(Continued)

FOREIGN PATENT DOCUMENTS

| | | |
|---|---|---|
| CN | 108578825 A | 9/2018 |
| CN | 216676744 U | 6/2022 |

(Continued)

OTHER PUBLICATIONS

PCT/US20/54757 filed Oct. 8, 2020 International Search Report and Written Opinion dated Feb. 17, 2021.

(Continued)

*Primary Examiner* — Philip R Wiest
*Assistant Examiner* — Peter Daniel Smith
(74) *Attorney, Agent, or Firm* — Rutan & Tucker LLP

(57) ABSTRACT

Briefly summarized, embodiments include apparatus and methods for removing an occlusion from an indwelling catheter. The system can include a pressurized fluid conduit for delivering pressurized fluid to an occlusion site, and ablating the occlusion. A negative pressure source in fluid communication with the catheter lumen can then aspirate the occlusion. The positive pressure source can provide a pulsed pressurized fluid to facilitate ablation. The system can also include tip tracking and tip location systems to ensure the pressurized fluid conduit does not extend beyond the catheter lumen, causing damage to the vasculature. The system can further include an ultrasound transducer, coupled with one or both of the catheter and the pressurized fluid conduit to provide ultrasonic wave energy to the occlusion to further facilitate ablation thereof.

21 Claims, 10 Drawing Sheets

(52) U.S. Cl.
CPC ................ *A61M 1/84* (2021.05); *A61M 1/85* (2021.05); *A61M 2202/04* (2013.01); *A61M 2205/0266* (2013.01); *A61M 2205/058* (2013.01); *A61M 2230/04* (2013.01)

(58) Field of Classification Search
CPC ............ A61M 2205/0266; A61M 1/87; A61M 2205/058; A61M 2230/04; A61M 5/145; A61M 2025/0019; A61M 2205/3538; A61M 2025/0073; A61B 5/72; A61B 5/318; A61B 5/7275; A61B 17/32
See application file for complete search history.

(56) References Cited

U.S. PATENT DOCUMENTS 4,509,947 A 4/1985 Lattin
4,698,058 A 10/1987 Greenfeld et al.
4,723,946 A 2/1988 Kay
4,955,862 A * 9/1990 Sepetka ............ A61M 25/0052 604/528
5,092,844 A 3/1992 Schwartz et al.
5,135,482 A * 8/1992 Neracher ......... A61B 17/32037 606/128
5,188,618 A 2/1993 Thomas
5,240,004 A 8/1993 Walinsky et al.
5,318,518 A 6/1994 Plechinger et al.
5,512,048 A 4/1996 Slettenmark
5,643,229 A 7/1997 Sinaiko
5,681,339 A 10/1997 McEwen et al.
5,730,806 A * 3/1998 Caimi ....................... B05B 7/24 134/22.12
5,741,244 A * 4/1998 Klaas .................. A61F 9/00825 606/4
5,964,004 A 10/1999 Bean
5,980,529 A * 11/1999 Strukel ............... A61F 9/00745 606/107
6,015,414 A * 1/2000 Werp ..................... A61B 90/10 606/108
6,027,572 A 2/2000 Labib et al.
6,044,855 A 4/2000 Monch
6,149,596 A 11/2000 Bancroft
6,183,450 B1 2/2001 Lois
6,283,719 B1 9/2001 Frantz et al.
6,423,266 B1 7/2002 Choperena et al.
6,585,934 B1 7/2003 Oberleitner et al.
6,681,783 B2 1/2004 Kawazoe
6,699,331 B1 3/2004 Kritzler
6,805,684 B2 10/2004 Bonnette et al.
6,958,056 B2 * 10/2005 Kadziauskas ........... A61M 1/84 604/294
7,005,012 B2 2/2006 Bourrelly et al.
7,179,269 B2 2/2007 Welch et al.
7,393,501 B2 7/2008 Zumeris et al.
7,494,484 B2 2/2009 Beck et al.
7,654,996 B2 2/2010 Lynn
7,669,600 B2 3/2010 Morejon
7,763,010 B2 7/2010 Evans et al.
7,775,215 B2 8/2010 Hassler, Jr. et al.
7,775,966 B2 8/2010 Dlugos et al.
7,829,029 B2 11/2010 Zumeris et al.
7,833,239 B2 11/2010 Nash
7,854,728 B2 12/2010 Boyle, Jr.
7,901,373 B2 * 3/2011 Tavger ............... A61C 17/0217 604/24
8,048,471 B2 11/2011 Nesbitt
8,177,919 B2 5/2012 Efinger et al.
8,246,752 B2 8/2012 Boyle, Jr.
8,256,057 B2 9/2012 Galantai et al.
8,394,068 B2 3/2013 Kosinski et al.
8,435,225 B2 5/2013 Courtney et al.
8,506,512 B2 8/2013 Aklog et al.
8,672,917 B2 3/2014 Sigg et al.
8,734,345 B2 5/2014 Deshpande et al.
8,741,069 B2 6/2014 Meyer
8,881,752 B1 11/2014 Fonteyn
8,943,633 B2 2/2015 Soh et al.
8,999,074 B2 4/2015 Zachar et al.
9,060,804 B2 6/2015 Meyer
9,095,286 B2 8/2015 Vazales et al.
9,254,371 B2 2/2016 Martin et al.
9,308,348 B2 4/2016 Mulvihill et al.
9,332,998 B2 5/2016 Ray et al.
9,532,844 B2 1/2017 Garvey et al.
9,707,325 B2 7/2017 Deeds
9,789,227 B1 10/2017 El-Hennawy et al.
9,848,904 B2 12/2017 Aljuri et al.
10,188,816 B2 * 1/2019 Khosrowshahi ..... A61M 11/006
10,188,831 B2 * 1/2019 Elberse .................. A61B 5/339
10,272,260 B2 * 4/2019 Kaplan .................. A61N 5/062
10,357,601 B1 7/2019 Flora et al.
11,020,572 B2 6/2021 Chappel et al.
11,154,677 B2 10/2021 Salinas et al.
2002/0111579 A1 8/2002 Moutafis et al.
2003/0109837 A1 6/2003 Mcbride-Sakal
2004/0073115 A1 4/2004 Horzewski et al.
2005/0096607 A1 5/2005 Beck
2006/0241459 A1 10/2006 Tai
2006/0241522 A1 10/2006 Chandraratna
2007/0179513 A1 8/2007 Deutsch
2007/0213645 A1 9/2007 Zumeris et al.
2007/0244423 A1 10/2007 Zumeris et al.
2008/0097206 A1 4/2008 Chomas et al.
2008/0097232 A1 * 4/2008 Rothenberg ............. A61B 5/06 600/509
2008/0267688 A1 10/2008 Busted
2009/0107529 A1 4/2009 Lin et al.
2009/0270815 A1 10/2009 Stamp et al.
2010/0204712 A1 8/2010 Mallaby
2010/0312084 A1 12/2010 Radojicic
2011/0004198 A1 1/2011 Hoch
2011/0105845 A1 5/2011 Gordon et al.
2011/0112564 A1 5/2011 Wolf
2011/0144540 A1 6/2011 Shen et al.
2011/0257593 A1 10/2011 Kalpin et al.
2012/0059286 A1 3/2012 Hastings et al.
2012/0302820 A1 11/2012 Carmeli et al.
2013/0190701 A1 * 7/2013 Kirn .................... A61J 15/0088 604/266
2014/0090195 A1 4/2014 Stadelman et al.
2014/0102445 A1 * 4/2014 Clement ................. A61M 1/77 128/202.13
2014/0150782 A1 6/2014 Vazales et al.
2014/0200554 A1 7/2014 Vitullo et al.
2014/0243789 A1 8/2014 Mehta et al.
2014/0257244 A1 9/2014 Johnston et al.
2014/0371725 A1 12/2014 Karimov et al.
2015/0080762 A1 * 3/2015 Kassab .................. A61B 5/062 600/585
2015/0231361 A1 8/2015 O'Keefe et al.
2015/0282821 A1 * 10/2015 Look .................. G06Q 30/0601 606/127
2015/0297176 A1 10/2015 Rincker et al.
2015/0305819 A1 10/2015 Krause
2015/0314074 A1 11/2015 Howlett et al.
2015/0343182 A1 12/2015 Vazales et al.
2015/0374401 A1 12/2015 Guggenheimer et al.
2016/0038647 A1 2/2016 Gittard et al.
2016/0175065 A1 6/2016 Gomez et al.
2016/0175560 A1 6/2016 Tallarida et al.
2017/0106128 A1 4/2017 Bagwell et al.
2017/0143880 A1 5/2017 Luxon et al.
2017/0265879 A1 9/2017 Washburn, II et al.
2017/0312548 A1 11/2017 Patil et al.
2017/0354777 A1 * 12/2017 Ofek .................. A61M 1/3659
2018/0001114 A1 1/2018 Li et al.
2018/0168668 A1 * 6/2018 Zheng ................... A61M 25/00
2018/0207322 A1 7/2018 Guo et al.
2019/0240472 A1 8/2019 Makey
2019/0290838 A1 9/2019 Ofek et al.
2020/0022777 A1 1/2020 Rama
2020/0046453 A1 2/2020 Vazales et al.
2020/0155003 A1 5/2020 Mitchell et al.

(56) References Cited

U.S. PATENT DOCUMENTS

| | | | | |
|---|---|---|---|---|
| 2020/0205845 | A1* | 7/2020 | Yang | A61M 25/0108 |
| 2021/0077714 | A1 | 3/2021 | Bodner | |
| 2021/0205611 | A1 | 7/2021 | Ta et al. | |
| 2021/0378593 | A1 | 12/2021 | Ofek et al. | |
| 2022/0071654 | A1 | 3/2022 | Jang et al. | |
| 2022/0142661 | A1 | 5/2022 | McLaughlin et al. | |
| 2022/0280984 | A1 | 9/2022 | Prakash et al. | |
| 2023/0001662 | A1 | 1/2023 | De Souza Neto et al. | |
| 2024/0148396 | A1 | 5/2024 | Prince | |
| 2024/0408348 | A1 | 12/2024 | Ahmed et al. | |
| 2026/0166293 | A1 | 6/2026 | Vergara et al. | |

FOREIGN PATENT DOCUMENTS

| | | | |
|---|---|---|---|
| EP | 3552552 | A1 | 10/2019 |
| EP | 3668411 | B1 | 1/2021 |
| WO | 9848711 | A1 | 11/1998 |
| WO | 2006071855 | A2 | 7/2006 |
| WO | 2007110870 | A2 | 10/2007 |
| WO | 2008097993 | A2 | 8/2008 |
| WO | 2015180730 | A1 | 12/2015 |
| WO | 17214120 | A1 | 12/2017 |
| WO | 2019098279 | A1 | 5/2019 |
| WO | 2021086569 | A1 | 5/2021 |
| WO | 2023288005 | A1 | 1/2023 |
| WO | 2024096882 | A1 | 5/2024 |
| WO | 2024102408 | A1 | 5/2024 |
| WO | 2024205563 | A1 | 10/2024 |
| WO | 2024254335 | A1 | 12/2024 |

OTHER PUBLICATIONS

EP 20882883.0 filed May 12, 2022 Extended European Search Report dated Feb. 8, 2024.

U.S. Appl. No. 17/865,146 filed Jul. 14, 2022 Non-Final Office Action dated Jul. 30, 2025.

U.S. Appl. No. 18/388,064, filed Nov. 8, 2023 Notice of Allowance dated Oct. 3, 2025.

Caroline Wall et al., "Catheter-related thrombosis: A practical approach", Journal of the Intensive Care Society, 2016, vol. 17(2) pp. 160-167, DOI: 10.1177/1751143715618683, (2016).

Jacquelyn Baskin et al., "Management of occlusion and thrombosis associated with longterm indwelling central venous catheters", Lancet. Jul. 11, 2009; 374(9684): 159. doi: 10.1016/S0140-6736(09)60220-8, pp. 1-23, (2009).

Kazuo Iwaya "The prevention of intravascular thrombosis based upon electric properties", 1st Department of Surgery, Nagoya University School of Medicine (Director: Prof. Yoshio Hashimoto), Nagoya J. med. Sci. 30: pp. 373-396, (1968).

PCT/US2022/037175 filed Jul. 14, 2022, International Search Report and Written Opinion dated Jan. 9, 2023.

PCT/US2022/048969 filed Nov. 4, 2022 International Search Report and Written Opinion dated May 8, 2023.

PCT/US2023/016320 filed Mar. 24, 2023 International Search Report and Written Opinion dated Dec. 8, 2023.

PCT/US2023/037024 filed Nov. 8, 2023 International Search Report and Written Opinion dated Feb. 22, 2024.

Ruchan Anbar et al. "Port catheter complications and thrombosis issues: assessment of 114 patients with port catheter implantation by single surgeon", Biomed Res Ther 2017, 4(12): pp. 1898-1910, DOI: 10.15419/bmrat.v4i12.40, ISSN: 2198-4093, www.bmrat.org, (2017).

Sibylle Machat et al., "Complications of central venous port systems: a pictorial review", Machat et al. Insights into Imaging (2019) 10:86 https://doi.org/10.1186/s13244-019-0770-2, pp. 1-12 , (2019).

U.S. Appl. No. 17/865,146, filed Jul. 14, 2022 Final Office Action dated Jan. 28, 2026.

U.S. Appl. No. 18/388,064, filed Nov. 8, 2023 Final Office Action dated Jul. 7, 2025.

Gil, B., Li, B., Gao, A., & Yang, G. Z. (2020). Miniaturized piezo force sensor for a medical catheter and implantable device. ACS applied electronic materials, 2(8), 2669-2677.

PCT/US2023/032853 filed Jun. 6, 2024 International Search Report and Written Opinion dated Oct. 1, 2024.

PCT/US2023/037024 filed Nov. 8, 2023 International Preliminary Report on Patentability dated Apr. 29, 2025.

U.S. Appl. No. 17/865,146, filed Jul. 14, 2022 Restriction Requirement dated May 19, 2025.

U.S. Appl. No. 18/388,064, filed Nov. 8, 2023 Non-Final Office Action dated Mar. 5, 2025.

U.S. Appl. No. 17/865,146 filed Jul. 14, 2022 Non-Final Office Action dated Jun. 17, 2026.

U.S. Appl. No. 18/736,357, filed Jun. 6, 2024 Non-Final Office Action dated Sep. 1, 2026.

* cited by examiner

FIG. 4A
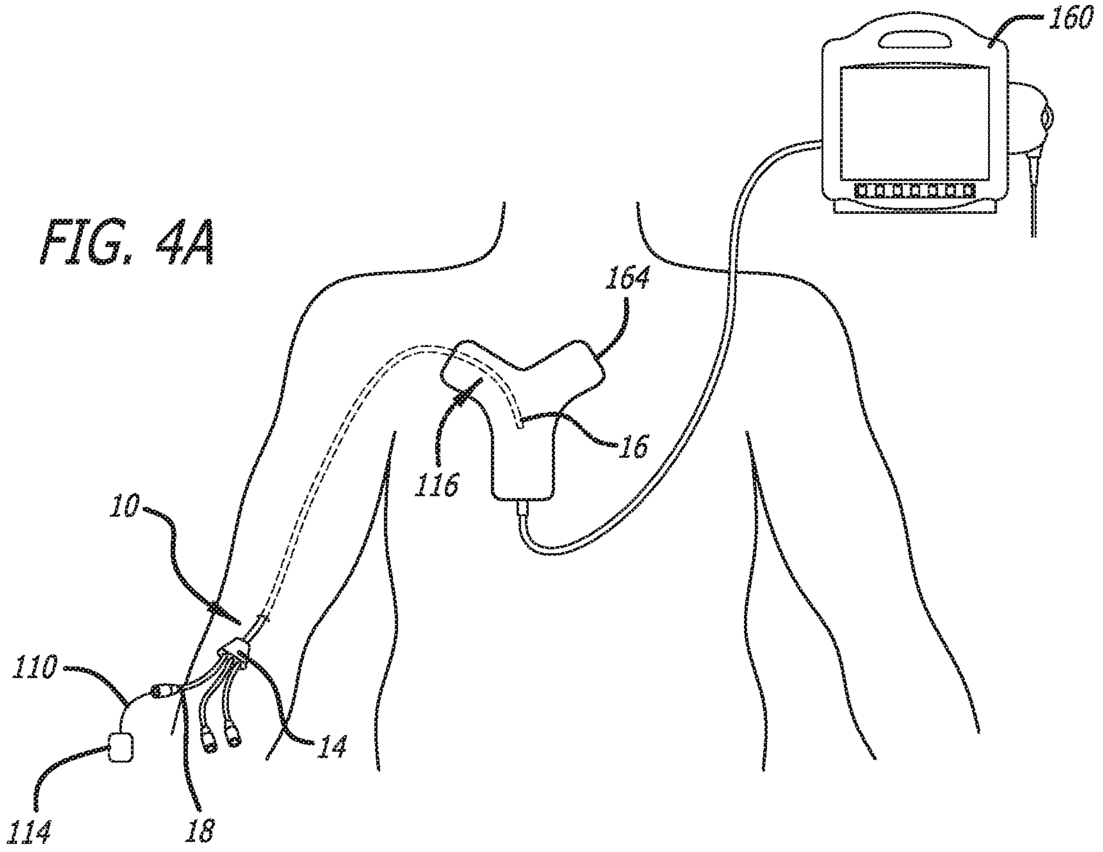
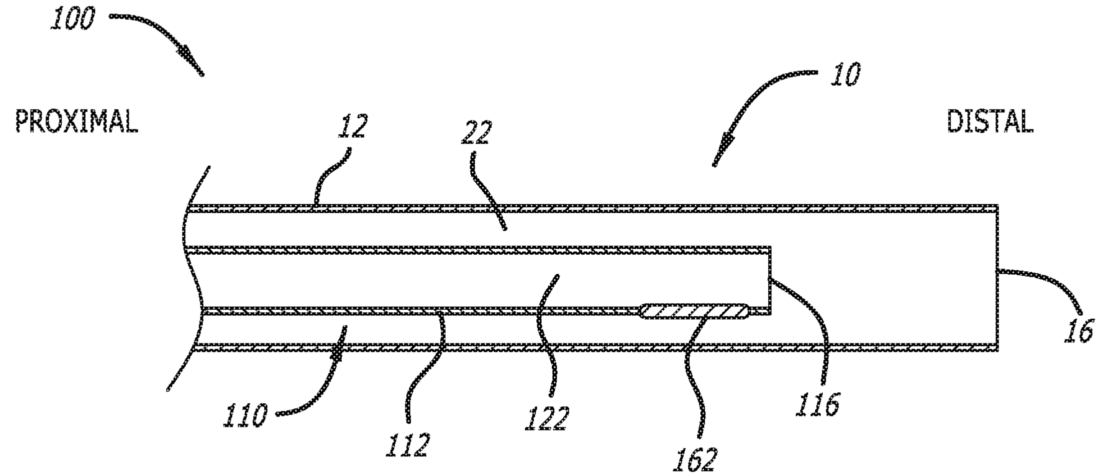
FIG. 4B

CATHETER PATENCY DEVICE

PRIORITY

This application claims the benefit of priority to U.S. Provisional Application No. 62/928,231, filed Oct. 30, 2019, which is incorporated by reference in its entirety into this application.

SUMMARY

Medium to long-term dwell catheters can incur occlusions caused by the buildup of biofilms, thrombosis, or the like. This results in the replacement of the catheter unless the occlusion is removed. Occluded catheters are currently treated with tissue plasminogen activator (tPA) to dissolve the occlusion. However, this can take upwards of 30 minutes to several hours, if successful at all.

Briefly summarized, embodiments disclosed herein are directed to apparatus and methods for disrupting and removing a catheter embolism while the catheter remains placed within the patient.

Disclosed herein an embolectomy system for restoring patency to an indwelling catheter having an occlusion disposed therein, the indwelling catheter including a catheter lumen extending from a proximal end of the indwelling catheter to a distal end of the indwelling catheter, the embolectomy system including a pressurized fluid conduit including a conduit body and a conduit lumen, the conduit body having an outer diameter less than an inner diameter of the catheter lumen to enable insertion and disposition of the pressurized fluid conduit in the catheter lumen, a positive pressure source in fluid communication with a proximal end of the conduit lumen, the positive pressure source providing a pressurized fluid, the conduit lumen directing the pressurized fluid into the occlusion in the catheter lumen, and a negative pressure source in fluid communication with the catheter lumen to aspirate the occlusion from the catheter lumen.

In some embodiments, the conduit lumen is in fluid communication with an opening disposed at a distal end of the conduit body, the pressurized fluid exiting the opening at an angle relative to a longitudinal axis of the conduit lumen. The opening disposed at the distal end of the conduit body includes a nozzle having one of a converging portion or a diverging portion. The pressurized fluid includes one of water and saline. The positive pressure source provides the pressurized fluid of between 0.1 psi to 400 psi. The positive pressure source provides the pressurized fluid of between 110 psi to 130 psi. The positive pressure source provides a pulsed pressurized fluid that varies in pressure between 0.1 psi and 400 psi at a rate of between 1 Hz to 150 Hz. The negative pressure source provides a medical vacuum of between −11 psi and −3 psi.

In some embodiments, the pressurized fluid conduit includes a reinforcement member extending through a portion of a wall of the pressurized fluid conduit. The reinforcement member includes a nitinol coil. In some embodiments, the embolectomy system further includes an ultrasound transducer coupled to the pressurized fluid conduit or the pressurized fluid and providing ultrasonic wave energy therethrough to the occlusion to fragment the occlusion. In some embodiments, the embolectomy system further includes an ultrasound transducer coupled to the catheter and providing ultrasonic wave energy through the catheter to the occlusion to fragment the occlusion. In some embodiments, the embolectomy system further includes a tip location system for tracking a magnetic element included with a distal portion of the pressurized fluid conduit. In some embodiments, the embolectomy system further includes an electrode included with a distal tip of the pressurized fluid conduit and configured for detecting an ECG signal, and a tip tracking system for receiving ECG data from the electrode and determining if the distal tip of the pressurized fluid conduit is proximate a distal tip of the indwelling catheter, or the occlusion has been cleared.

In some embodiments, the embolectomy system further includes a first electrode and a second electrode included with a distal portion of the pressurized fluid conduit, the first electrode configured for detecting an intra-luminal conductance at a first position and the second electrode configured for detecting an intra-luminal conductance at a second position, and a lumen localization system for measuring changes in relative conductance between the first position and the second position to determine a change in intraluminal cross-sectional area, indicating a distal tip of the pressurized fluid conduit is proximate a distal tip of the indwelling catheter.

Also disclosed is a method of removing an occlusion from a catheter lumen of an indwelling catheter, the method including providing an embolectomy system having a pressurized fluid conduit including a conduit lumen, a positive pressure source in fluid communication with the conduit lumen, the pressurized fluid source providing a pressurized fluid, and a negative pressure source in fluid communication with a collection container and the catheter lumen, introducing the pressurized fluid conduit into the catheter lumen until a distal end of the pressurized fluid conduit is proximate the occlusion, applying the pressurized fluid through the pressurized fluid conduit lumen into the occlusion to fragment the occlusion, and aspirating the occlusion proximally through the catheter lumen to the collection container.

In some embodiments, the pressurized fluid is between 0.1 psi and 400 psi. In some embodiments, applying the pressurized fluid further includes applying a pulsed pressurized fluid that varies in pressure between 0.1 psi and 400 psi at a rate of between 1 Hz to 150 Hz. In some embodiments, the method further includes directing the pressurized fluid at an angle relative to a longitudinal axis of the conduit lumen. The angle is between 5° and 90°. In some embodiments, the method further includes providing ultrasonic wave energy through one of the pressurized fluid conduit, the catheter, or the pressurized fluid to fragment the occlusion. In some embodiments, the method further includes tracking a magnetic element included with a distal portion of the pressurized fluid conduit to determine a location of a tip of the pressurized fluid conduit. In some embodiments, the method further includes detecting an ECG signal strength at a distal portion of the pressurized fluid conduit and determining if the distal portion is proximate a distal tip of the indwelling catheter, or the occlusion has been cleared. In some embodiments, the method further includes detecting an intra-luminal conductance at a first position and an intra-luminal conductance at a second position and measuring a change in relative conductance to determine a change in intraluminal cross-sectional area between the first position and the second position, indicating a distal tip of the pressurized fluid conduit is proximate a distal tip of the indwelling catheter.

Also disclosed is an embolectomy system for removing an occlusion from an indwelling catheter including, a pressurized fluid conduit including a first conduit lumen and a second conduit lumen, a positive pressure source in fluid communication with the first conduit lumen, the positive pressure source providing a pressurized fluid for ablating the occlusion, and a negative pressure source in fluid communication with the second conduit lumen, the negative pressure source providing a negative pressure for aspirating the occlusion from the indwelling catheter.

In some embodiments, the first conduit lumen includes an opening at the distal end that directs the pressurized fluid at an angle relative to a longitudinal axis of the first conduit lumen. The first conduit lumen includes a nozzle disposed at the distal end, and configured for developing a jet of pressurized fluid as the pressurized fluid passes therethrough. The positive pressure source provides a pulsed pressurized fluid that varies in positive pressure between 0.1 psi and 400 psi at a rate of between 1 Hz to 150 Hz. One of the first conduit lumen or the second conduit lumen includes a reinforcement member. The reinforcement member includes a nitinol coil. In some embodiments, the embolectomy system further includes a tip location system for tracking a magnetic element included with a distal portion of the pressurized fluid conduit. In some embodiments, the embolectomy system further includes an electrode included with a distal tip of the pressurized fluid conduit and configured for detecting an ECG signal, and a tip tracking system for receiving ECG data from the electrode and determining if the distal tip of the pressurized fluid conduit is proximate a distal tip of the indwelling catheter, or the occlusion has been cleared.

In some embodiments, the embolectomy system further includes a first electrode and a second electrode included with a distal portion of the pressurized fluid conduit, the first electrode configured for detecting an intra-luminal conductance at a first position and the second electrode configured for detecting an intra-luminal conductance at a second position, and a lumen localization system for measuring changes in relative conductance between the first position and the second position to determine a change in intraluminal cross-sectional area, indicating a distal tip of the pressurized fluid conduit is proximate a distal tip of the indwelling catheter. In some embodiments, the embolectomy system further includes an ultrasound transducer coupled to one of the pressurized fluid conduit, the indwelling catheter, or the pressurized fluid and configured to provide ultrasonic wave energy therethrough to the occlusion to fragment the occlusion.

Also disclosed is a method of removing an occlusion from a catheter lumen of an indwelling catheter including, providing an embolectomy system having a stylet extending from a proximal end to a distal end, the stylet including a stent retrieval structure disposed at the distal end thereof, and a negative pressure source in fluid communication with the catheter lumen and configured for aspirating the occlusion from the catheter lumen, introducing the stylet into the catheter lumen until the stent retrieval structure is proximate the occlusion, grasping the occlusion using the stent retrieval structure to fragment and withdraw a portion of the occlusion in a proximal direction, and aspirating the occlusion proximally through the catheter lumen to a collection container.

In some embodiments, the method further includes an ultrasound transducer coupled to the stylet and configured to provide ultrasonic wave energy therethrough to the occlusion to fragment the occlusion.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 4A-4B illustrate an embolectomy system including a tip location system for restoring patency to an implanted catheter, in accordance with embodiments disclosed herein.

DESCRIPTION

Figure 1:
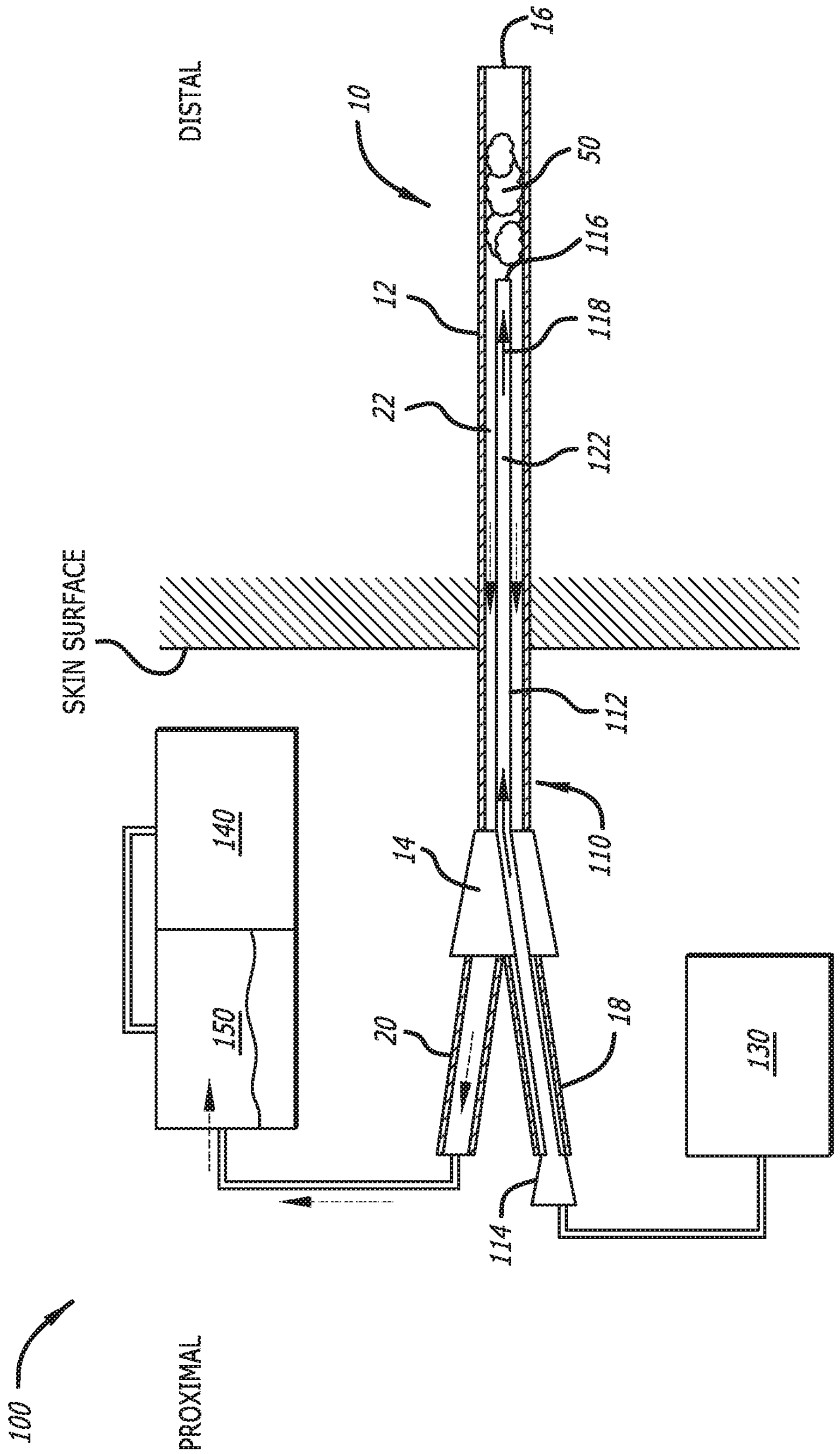
FIG. 1 illustrates an embolectomy system for restoring patency to an implanted catheter, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a “proximal length” of, for example, the catheter includes a length of the catheter intended to be near the clinician when the catheter is used on the patient. A “proximal end” of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to “distal,” a “distal portion” or a “distal end portion” of, for example, a catheter disclosed herein includes a portion of the catheter intended to be near or in a patient when the catheter is used on the patient. Likewise, a “distal length” of, for example, the catheter includes a length of the catheter intended to be near or in the patient when the catheter is used on the patient. A “distal end” of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, a longitudinal axis extends substantially parallel to an axial length of a catheter 10. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

FIG. 1 shows an exemplary embolectomy system (“system”) 100 for clearing an occlusion from an indwelling catheter, e.g. catheter 10. Exemplary indwelling catheters include single lumen or multilumen central venous catheters (“CVC”), peripherally inserted central catheters (“PICC”), implanted ports, midline catheters, urinary, arterial, balloon catheters, or the like. Although it will be appreciated that embodiments disclosed herein can be used with any tubular device.

The catheter 10 includes an elongate tubular body 12 defining a lumen 22 and extends from a catheter hub 14 disposed at a proximal end, to a distal tip 16 that includes an opening communicating with the lumen 22. A distal portion of the catheter body 12 can be disposed within a patient, for example within a vasculature of the patient. A proximal portion of the catheter body 12, including the catheter hub 14 can be disposed outside of the patient. Optionally, the hub 14 includes one or more extension legs extending from a proximal end thereof and communicating with one or more lumens of the catheter 10. As shown in FIG. 1, a first extension leg 18 and a second extension leg 20 both communicate with the single lumen of the catheter body 10, although it will be appreciated that other configurations are also contemplated.

As shown in FIG. 1 an occlusion 50, e.g. a thrombosis, obstructs flow at a distal portion of the lumen 22 of the catheter body 12. Although an exemplary occlusion 50 is provided as a total occlusion of the catheter, it will be appreciated that the occlusion 50, as used herein, can also include partial occlusions of the catheter 10, as well as thin biofilms disposed on an inner or outer surface of the catheter 10. Embodiments disclosed herein include apparatus and methods to clear the occlusion 50 with the catheter 10 remaining disposed within the patient.

As shown in FIG. 1, in an embodiment, a pressurized fluid conduit 110 is inserted into the lumen 22 by way of the first extension leg 18. It will be appreciated that the pressurized fluid conduit 110 can also be introduced to the lumen 22 through various structures such as hemostasis valves, 3-way valves, flap valves, duckbill valves, combinations thereof, or the like. The pressurized fluid conduit 110 includes a conduit body 112 extending from a hub 114 disposed at a proximal end, to an opening 106 disposed at a distal tip 116, and defines a conduit lumen 122. The hub 114 is in fluid communication with a positive pressure source 130, for example a high pressure pump that delivers water, saline, or similar positive pressurized fluid. In an embodiment, the fluid further includes various active ingredients, such as plasminogen activator (tPA) or the like, to further assist in removing the occlusion 50. A negative pressure source 140 is coupled a collection container 150 and the second extension leg 20, so as to be in fluid communication with lumen 22 of the catheter body 12.

In use, when an occlusion 50 is detected within the lumen 22, the pressurized fluid conduit 110 can be introduced to the lumen 22 and advanced so that a distal tip 116 is proximate to the occlusion 50. The positive pressure source 130 provides a high pressure fluid through the conduit lumen 122 and applies a jet of high pressure fluid to the occlusion 50, as indicated by the solid arrows. The jet of high pressure fluid can disrupt, ablate or fragment the occlusion 50. Concurrently, the negative pressure source 140 applies a suction to the lumen 22 of the catheter 10. The negative pressure source 140 can aspirate any fragmented portions of the occlusion 50 to the collection container 150. Advantageously, the diameter of the catheter lumen 22 is larger than the outer diameter of the conduit body 112 and allows the occlusion 50, or portions thereof, to pass proximally as indicated by the dashed arrows.

In an embodiment, the positive pressure source 130 provides a pressurized fluid of between 0.1 psi to 400 psi, with a preferred pressure of between 110 psi to 130 psi. In an embodiment, the positive pressure source 130 provides different flow rates of pressurized fluid of between 0.1 ml per sec and 15 ml per sec, further the different flow rates can be selected by the clinician. In an embodiment, the positive pressure source 130 provides a pulsed pressurized fluid. The pulsed pressurized fluid varies in pressure from between 0.1 psi to 400 psi, with a preferred pressure variation of between 20 psi to 50 psi. In an embodiment, the pulsed pressurized fluid varies at a rate of 1 Hz to 150 Hz. In an embodiment, the pulsed pressurized fluid varies at a rate of up to 20 kHz. In an embodiment, the pulsed pressurized fluid varies at a rate of above 20 kHz. Advantageously, the pulsed pressurized fluid can further disrupt the occlusion 50 facilitating aspiration thereof. It will be appreciated that pressures, flow rates, and frequencies outside of the ranges described herein, are also contemplated.

In an embodiment, the negative pressure source 140 provides a negative pressure relative to ambient atmospheric pressure, i.e. substantially 1 atmosphere or 15 psi. In an embodiment, the negative pressure source provides a medical vacuum, i.e. a relative pressure of between −11 psi and −3 psi. In an embodiment, a user is able to control the pressure, flow rate, negative pressure, or combinations thereof to ensure occlusion 50 can be removed without damaging the catheter 10. Further details and embodiments of the system 100, as well as fluid pressures, flow rates, and pulsed pressurized fluid frequencies can be found in U.S. Pat. No. 10,322,230, which is herein incorporated by reference in its entirety.

Figure 2A:
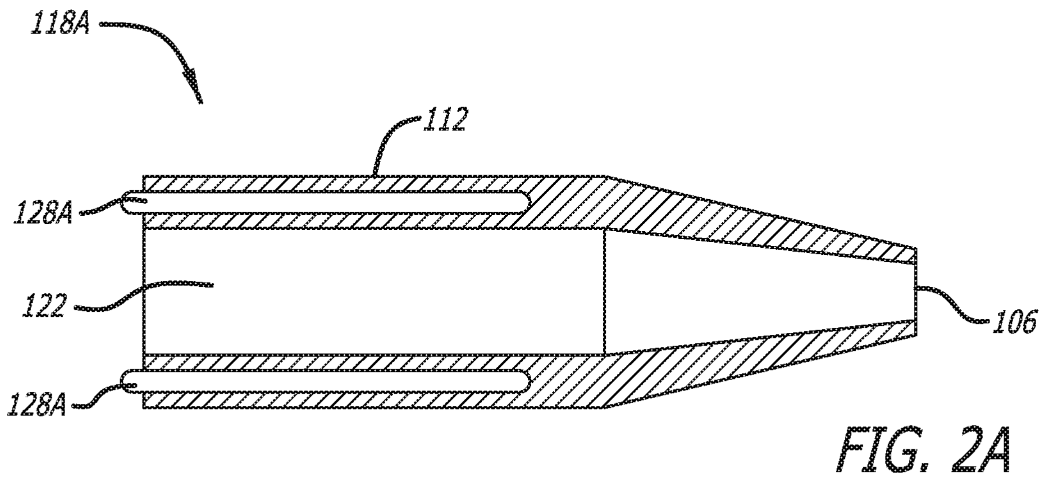
FIGS. 2A-2E illustrates embodiments of nozzles for the embolectomy system shown in FIG. 1, in accordance with embodiments disclosed herein.
Figure 2B:
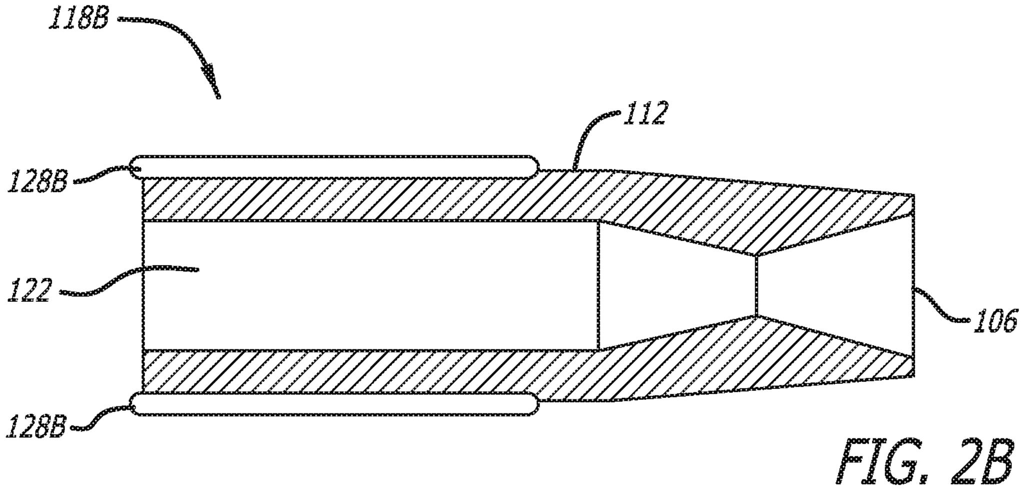
Figure 2C:
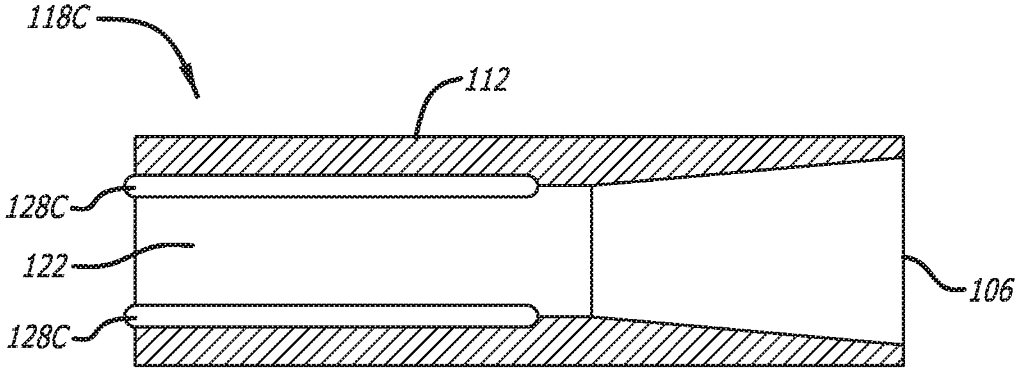

In an embodiment, the distal end tip of the pressurized fluid conduit 110 includes a nozzle 118. As used herein, the term "nozzle" includes a structure that modifies the flow of a fluid therethrough. FIGS. 2A-2E show cross-section side views of exemplary embodiments of nozzle 118 that can be included with the pressurized fluid conduit 110. FIG. 2A shows a converging nozzle 118A. FIG. 2B shows a converging-diverging nozzle 118B. FIG. 2C shows a diverging nozzle 118C. The converging sections of nozzles 118A-118B can accelerate the fluid as it passes through the nozzle. The diverging sections of nozzles 118B-118C can facilitate a smooth introduction of the fluid jet produced by the nozzle, with that of the relatively static fluid surrounding and distal of the nozzle.

Figure 2D:
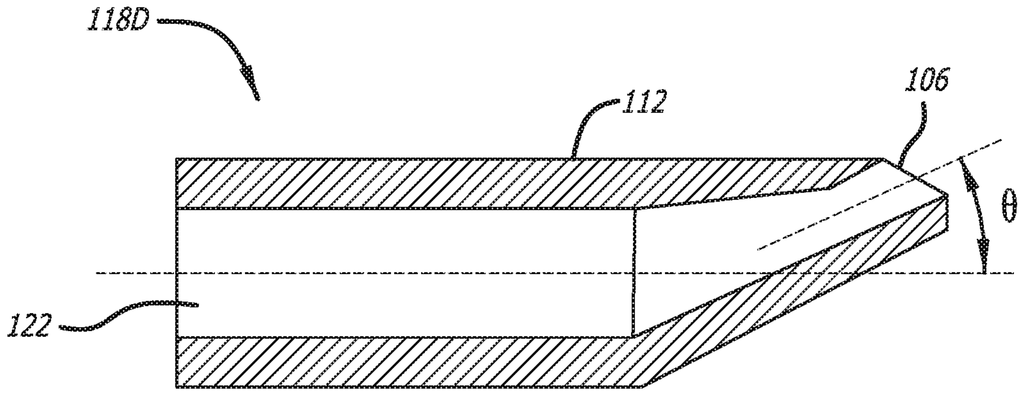
Figure 2E:
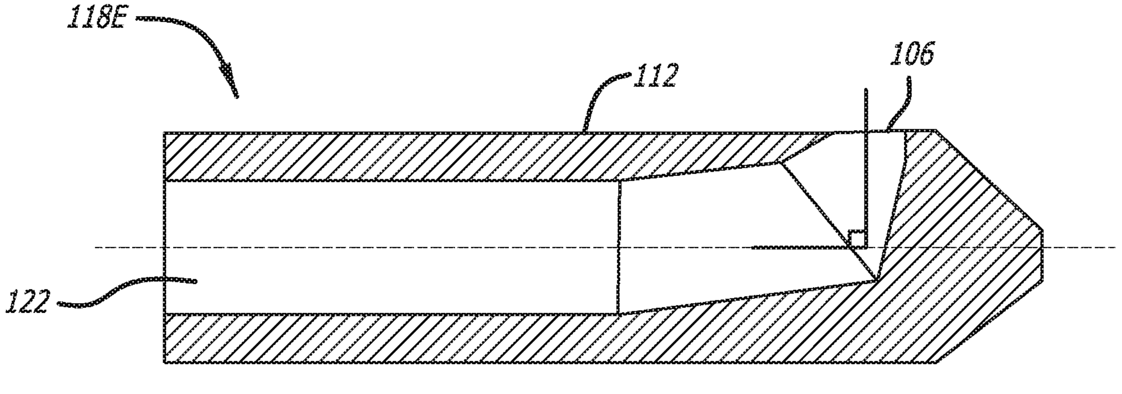

In an embodiment, as shown in FIGS. 2D-2E, the nozzle 118 can angle the jet of pressurized fluid, exiting the distal opening 106, relative to the longitudinal axis of the pressurized fluid conduit 110. As shown in FIG. 2D, the nozzle 118D angles the jet of the pressurized fluid to exit from the distal opening 106 at an angle θ. Angle θ can be between 5° and 85°, with a preferred embodiment being substantially 45°. As shown in FIG. 2E, the nozzle 118E angles the jet of the pressurized fluid to exit from the distal opening 106 at an angle of 90°, substantially perpendicular to the longitudinal axis of the pressurized fluid conduit 110.

In an embodiment, a wall of the conduit body 112 includes a reinforcement member configured to prevent the conduit body 112 from bursting when receiving pressurized fluid. For example, as shown in FIG. 2A, the conduit body 112 can include a reinforcement member 128A disposed within a wall of the conduit body 112. As shown in FIG. 2B, the conduit body 112 can include a reinforcement member 128B disposed on an outer surface of the conduit body 112. As shown in FIG. 2C, the conduit body 112 can include a reinforcement member 128C disposed on an inner wall of the lumen 122 of the conduit body 112. In an embodiment the reinforcement member 128 extends along at least a portion of the conduit body 112. In an embodiment, the reinforcement member extends substantially the entire length of the conduit body 112, from a proximal end to a distal end of the device 110. In an embodiment the reinforcement member is formed of a metal or polymer, for example nitinol, nylon, or the like. In an embodiment, the reinforcement member is a nitinol coil that extends about the longitudinal axis of the lumen 122 and is co-extruded with the device 110.

Figure 3:
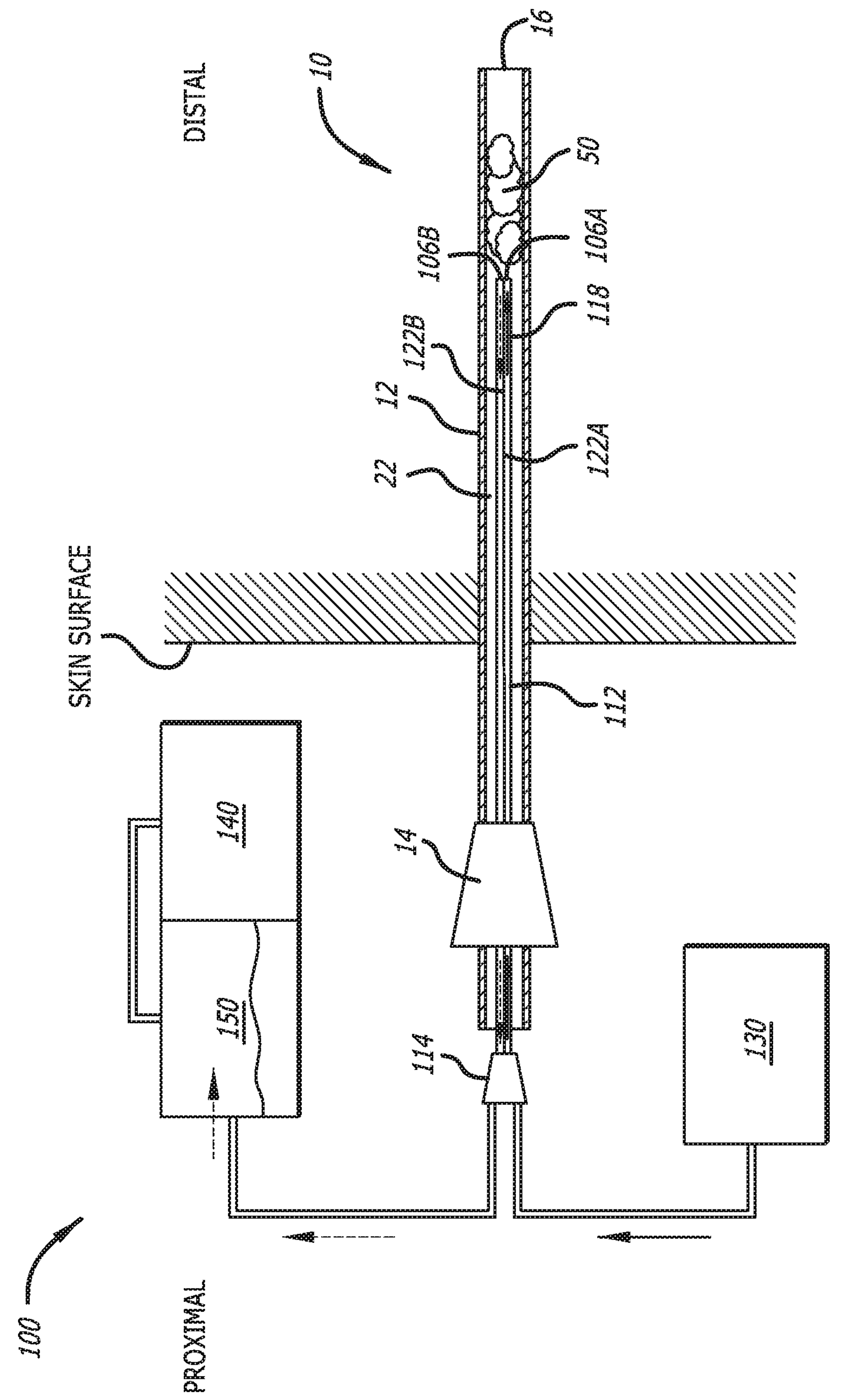
FIG. 3 illustrates an embolectomy system for restoring patency to an implanted catheter, in accordance with embodiments disclosed herein.

As shown in FIG. 3, in an embodiment, the pressurized fluid conduit 110 includes a dual-lumen conduit body 112. A positive pressure source 130 can be in fluid communication with a first conduit lumen 122A to deliver a pressurized fluid to a first distal opening 106A and disrupt the occlusion 50, as described herein. A negative pressure source 140 can be in fluid communication with a second conduit lumen 122B and a second distal opening 106B. The second conduit lumen 122B can aspirate portions of the occlusion 50 that have been dislodged by the pressurized fluid and remove the occlusion 50 proximally to the collection container 150, as described herein.

Advantageously, the conduit body 112 can include materials and structures that are different from the catheter 10 and can sustain a lower negative pressure while maintaining the patency of the second conduit lumen 122B and preventing any damage to the catheter 10. For example, the conduit body 112 can include a reinforcement member 128, as described herein, that prevents the second conduit lumen 122B from collapsing under a negative pressure. This allows for a harder negative pressure (i.e. lower pressure) to be applied to draw the occlusion 50 proximally. In an embodiment, the cross-sectional diameter of the first conduit lumen 122A and the second conduit lumen 122B can be the same. In an embodiment, the cross-sectional diameter of the first conduit lumen 122A and the second conduit lumen 122B can be different. In an embodiment, the first distal opening 116A, second distal opening 116B, or combinations thereof can include a nozzle 118, as described herein.

As shown in FIGS. 4A-4B, in an embodiment, the embolectomy system 100 further includes a tip location system ("TLS") 160 that tracks the location of the distal tip 116 of the pressurized fluid conduit 110 within the patient. Advantageously, TLS 160 can determine the location of the pressurized fluid conduit 110 within the catheter 10 to ensure that the pressurized fluid conduit 110 is traveling in the correct direction. In an embodiment, the distal tip 116 of the pressurized fluid conduit 110 includes a magnetic element 162, for example a permanent magnet element or an electromagnetic element, which emits a magnetic field. The TLS 160 includes a sensor 164 disposed on a skin surface of the patient and configured to detect the magnetic field of the magnetic element 162. The TLS 160 then detects and determines the location of the magnetic element 162, and tip 116, relative to the sensor 164. In an embodiment, the sensor 164 is positioned proximate a distal tip 16 of the catheter 10 and the TLS 160 indicates the approach of the tip 116 relative to the sensor 164. In an embodiment, the sensor 164 is positioned proximate the tip 116 of the pressurized fluid conduit 110 and is moved across the skin surface of the patient as adjacent the tip 116, as the pressurized fluid conduit 110 is advanced through the catheter 10.

Figure 5A:
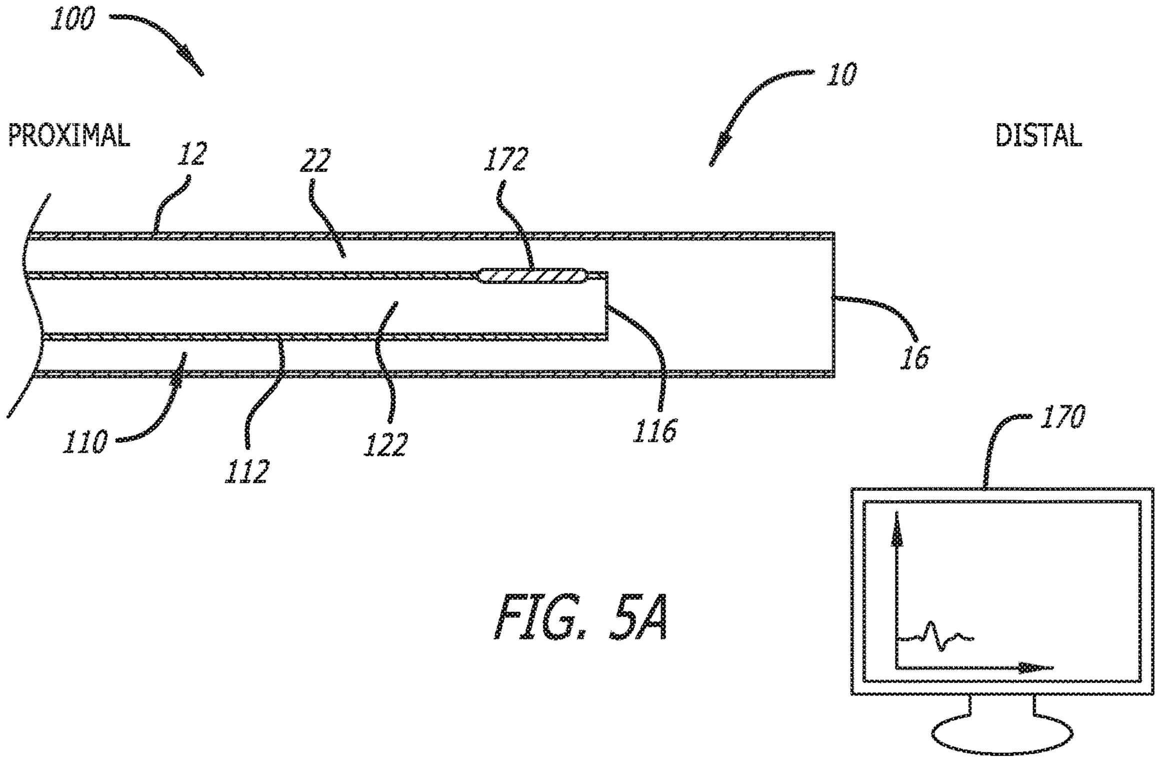
FIGS. 5A-5B illustrates an embolectomy system including a tip tracking system for restoring patency to an implanted catheter, in accordance with embodiments disclosed herein.
Figure 5B:
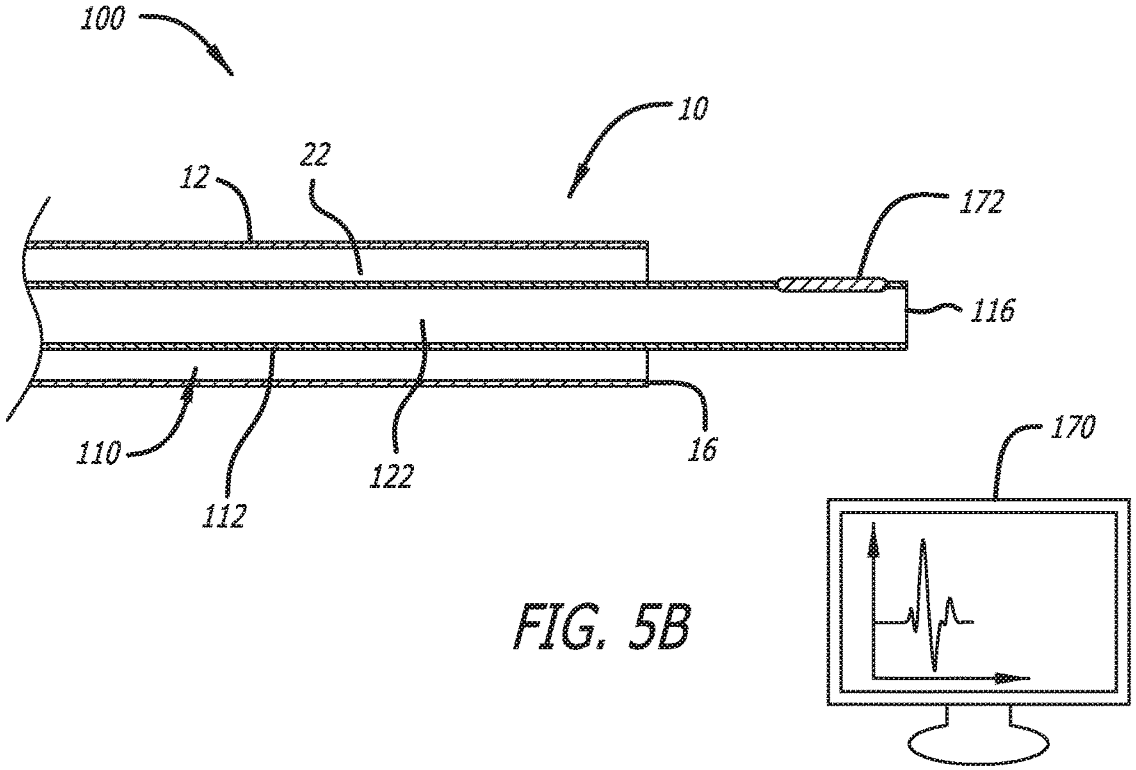

In an embodiment, the embolytic system 100 further includes a tip tracking system 170 that detects if the occlusion has been cleared or detects if the tip 116 of the pressurized fluid conduit 110 is proximate the distal tip of the catheter 10. To note, if the pressurized fluid is exposed to the vasculature of the patient, the forces can potentially cause damage to otherwise healthy tissues. Accordingly, tracking the location of the tip 116 relative to the catheter tip 16 can be important. As shown in FIGS. 5A-5B, the tip of the pressurized fluid conduit 110 includes an electrode 172. The electrode 172 is coupled, either wired or wirelessly, with a tip tracking system 170. The electrode 172 detects an ECG wave of the patient. As shown in FIG. 5A, the ECG wave will be attenuated or absent when the tip 116 of the pressurized fluid conduit 110 is disposed within the lumen 22 of the catheter, and/or blocked by the occlusion 50. As shown in FIG. 5B, if occlusion 50 is cleared and/or the tip 116 of the pressurized fluid conduit 110 extends beyond the distal tip 16 of the catheter 10, into the vasculature of the patient, the ECG wave will be relatively unattenuated. This change in ECG wave signal can be detected and interpreted by the tip tracking system 170 and alert the clinician if the occlusion 50 has been cleared, or if the conduit tip 116 is proximate to, or distally beyond, the catheter tip 16.

Figure 5C:
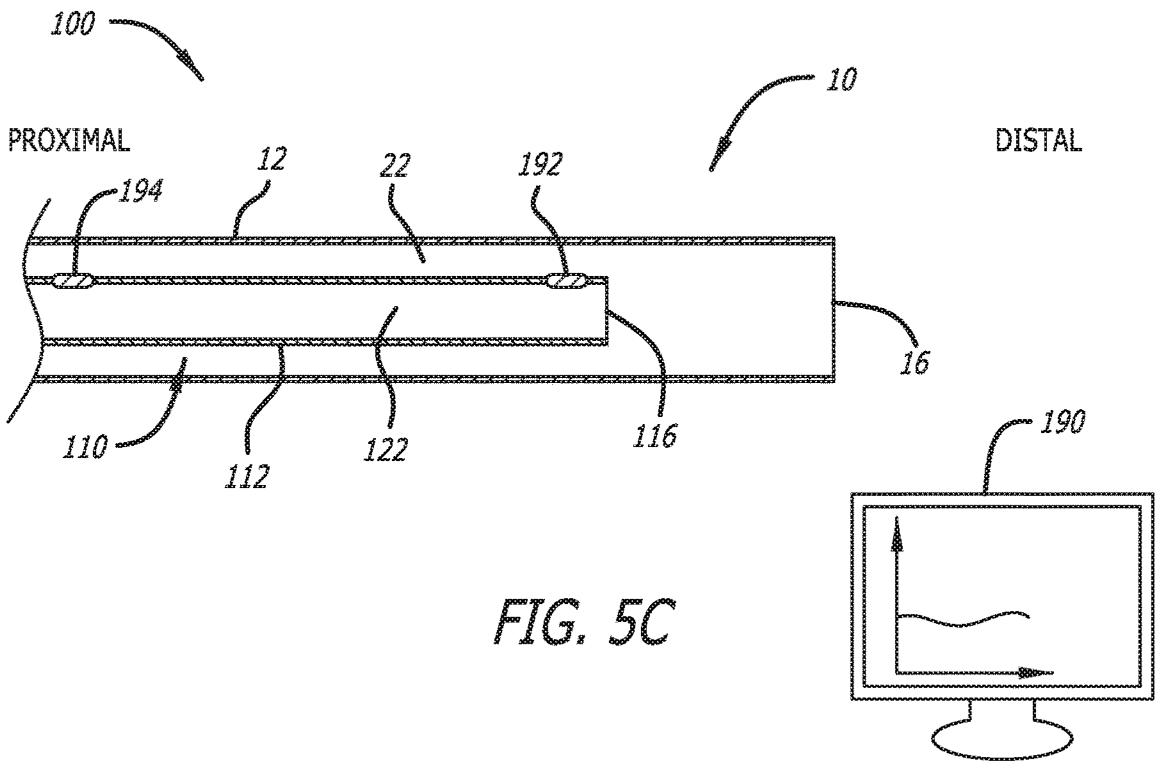
FIGS. 5C-5D illustrates an embolectomy system including a lumen localization system for restoring patency to an implanted catheter, in accordance with embodiments disclosed herein.
Figure 5D:
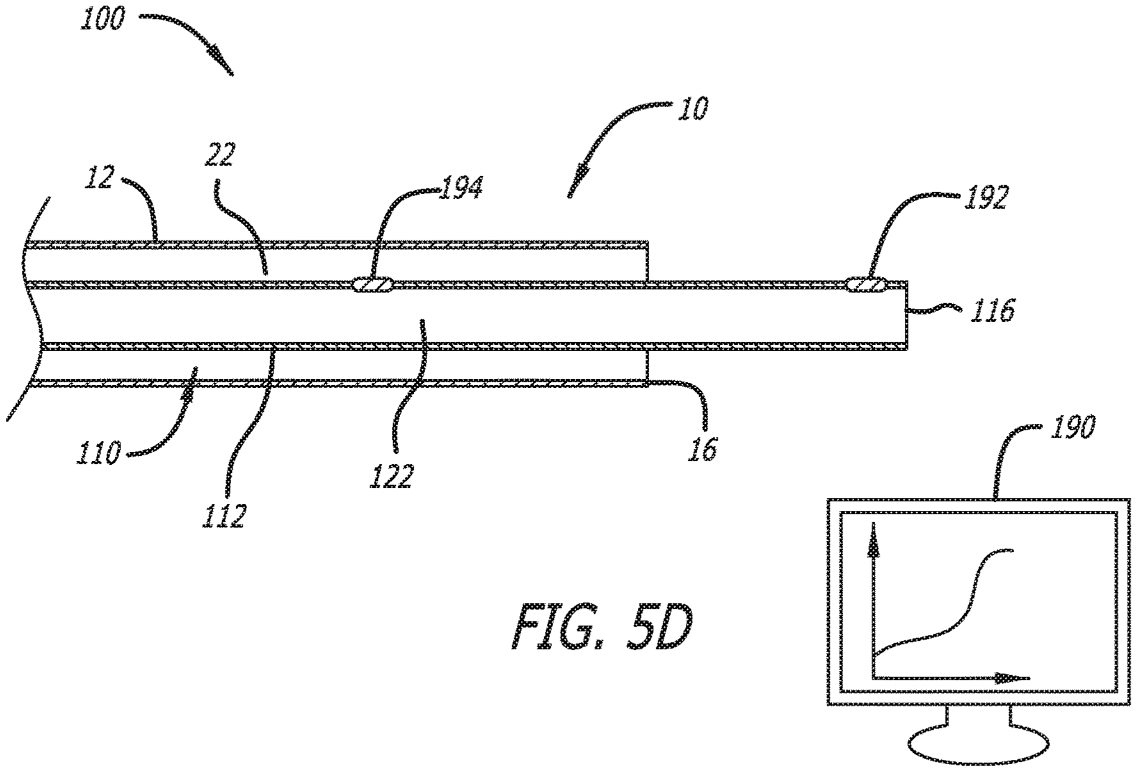

In an embodiment, the embolytic system 100 further includes a lumen localization system 190 that determines intra-lumen conductance, intra-lumen impedance, cross-sectional area, cross-sectional profiles, or combinations thereof. As shown in FIGS. 5C-5D, the pressurized fluid conduit 110 includes a first electrode 192 and a second electrode 194 that collect relative conductance values at two different positions along the pressurized fluid conduit 110. Each electrode of the pair of electrodes serves as both an excitation function and a detection function. It will be appreciated that embodiments can include more than two electrodes and fall within the scope of the present invention. A processor receives information from the first and second electrodes 192, 194 and measures any changes in relative conductance between the first electrode 192 and the second electrode 194 to determine any change in intraluminal cross-sectional area or profile. This change in relative conductance or impedance can be detected and interpreted by the lumen localization system 190 and alert the clinician that the conduit tip 116 is proximate to, or distally beyond, the catheter tip 16, where the pressurized fluid conduit 110 can potentially cause damage to the tissues of the patient. Similarly, the lumen localization system 190 can detect a decrease in cross-sectional lumen area, indicating a partial occlusion of the catheter lumen 22. Accordingly, the catheter lumen can be treated, as described herein, to remove the partial occlusion.

It will be appreciated that the embolytic system 100 can include the tip location system ("TLS") 160, the tip tracking system 170, the lumen localization system 190 as described herein, embodiments thereof, or combinations thereof. Further details and embodiments of the tip location system 160, tip tracking system 170, and lumen localization system 190, can be found in U.S. Pat. Nos. 8,388,541, 8,781,555, 8,849,382, 9,445,743, 9,456,766, 9,492,097, 9,521,961, 9,554,716, 9,636,031, 9,649,048, 10,159,531, 10,172,538, 10,413,211, 10,449,330, 10,524,691, 10,751,509, U.S. Publication No. 2015/0080762, and U.S. Publication No. 2018/0116551, each of which are incorporated by reference in their entirety into this application.

Figure 6:
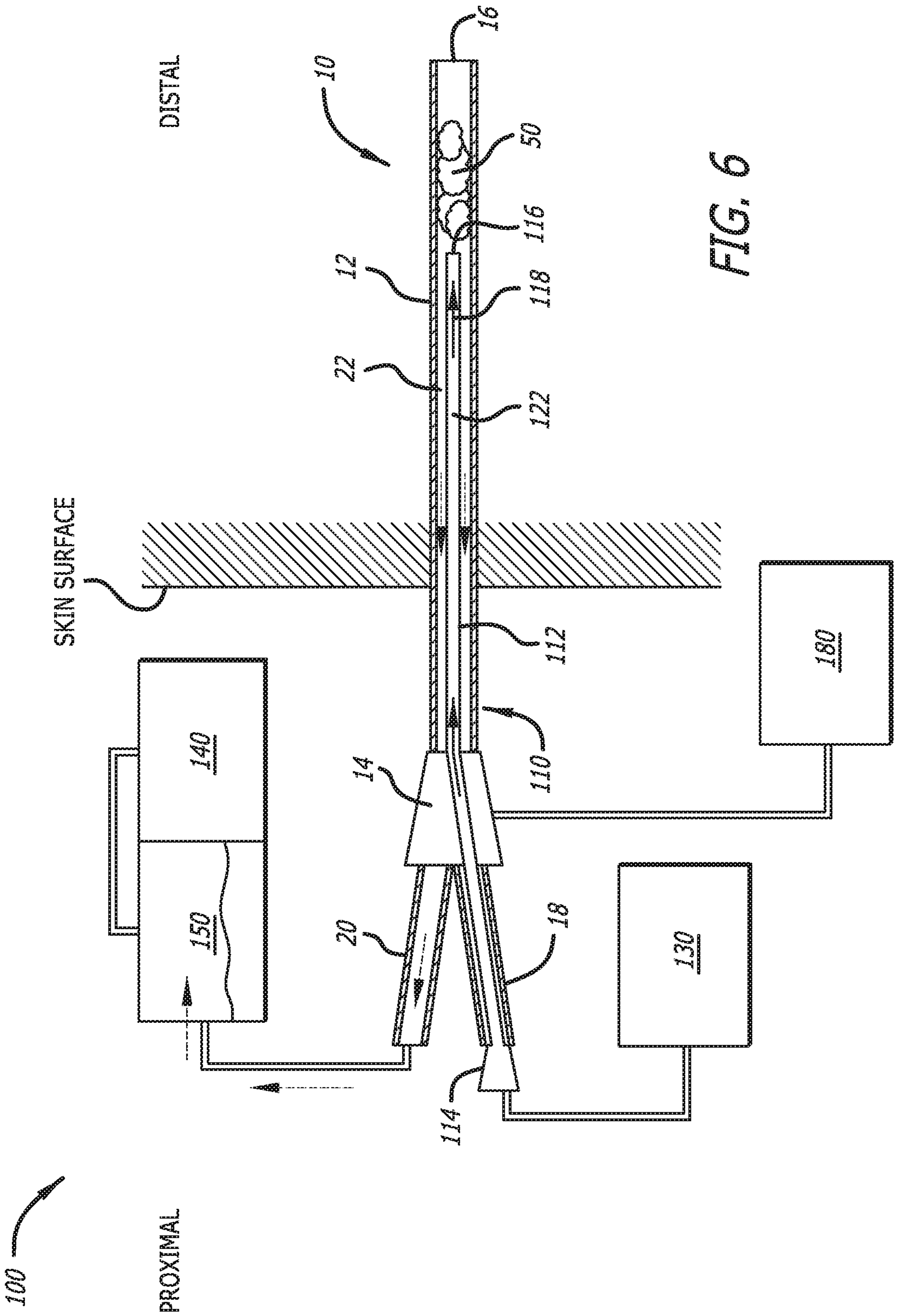
FIG. 6 illustrates an embolectomy system for restoring patency to an implanted catheter, in accordance with embodiments disclosed herein.

As shown in FIG. 6, in an embodiment, the embolectomy system 100 includes an ultrasound transducer 180 coupled with the catheter 10, hub 14, catheter body 12, or combinations thereof. The ultrasound transducer 180 introduces ultrasonic wave energy directly to the catheter body 12. The wave energy can include longitudinal waves, transverse waves, surface waves, or combinations thereof. The wave energy travels along the catheter 10 to the occlusion site. The ultrasonic wave energy provides thrombolytic effects directly to the occlusion 50, and dislodges the occlusion 50 from the walls of the catheter lumen 22, breaks up the occlusion 50, or combinations thereof. Advantageously, the ultrasound energy also dislodges any biofilm build on the walls of the lumen 22. The occlusion 50 can then be aspirated as described herein.

Figure 7:
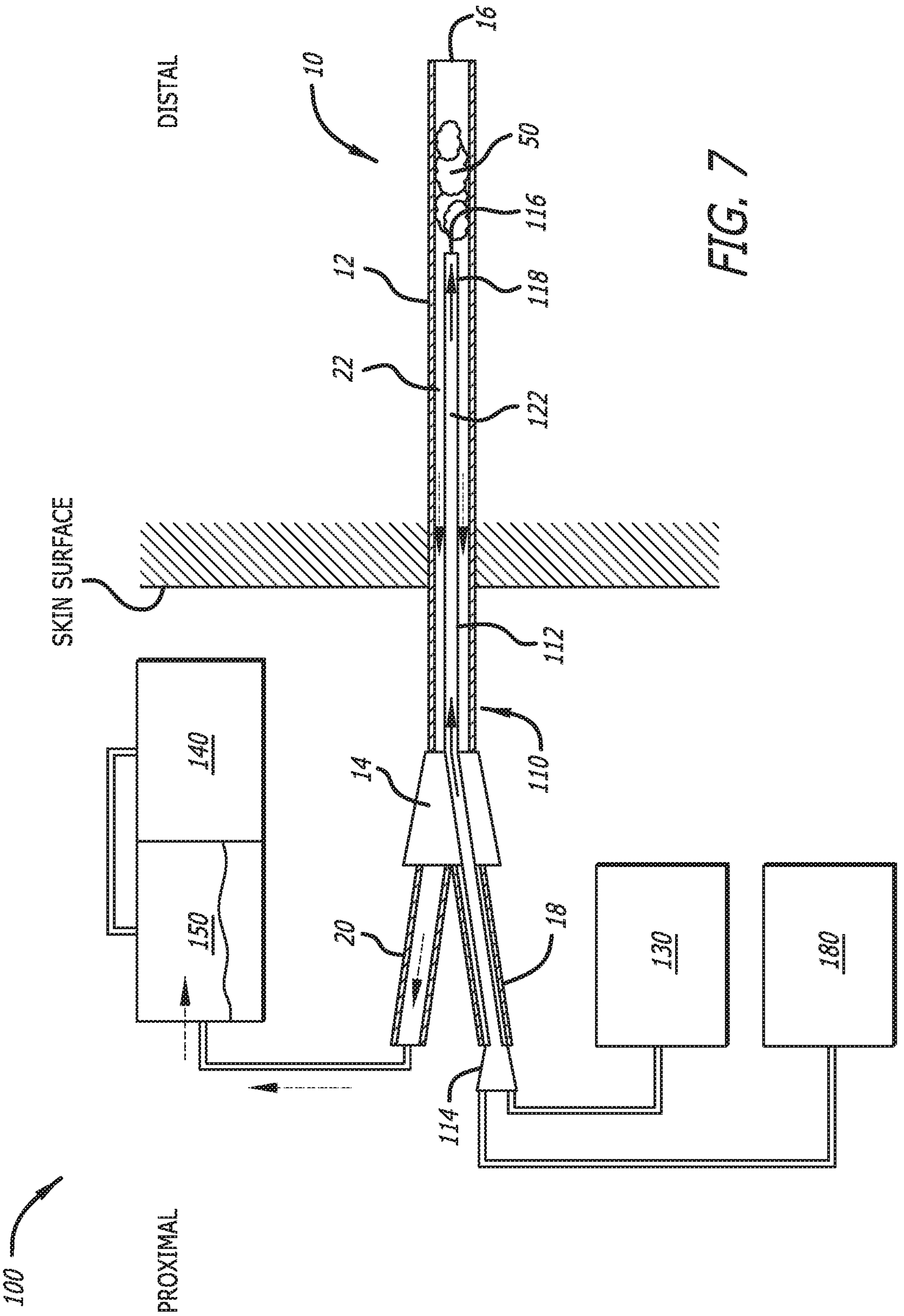
FIG. 7 illustrates an embolectomy system for restoring patency to an implanted catheter, in accordance with embodiments disclosed herein.

As shown in FIG. 7, in an embodiment, the embolectomy system 100 includes an ultrasound transducer 180 coupled with the pressurized fluid conduit 110, hub 114, conduit body 112, or combinations thereof. The ultrasound transducer 180 introduces ultrasonic wave energy directly to the conduit body 112. The wave energy can include longitudinal waves, transverse waves, surface waves, or combinations thereof. The wave energy travels along the pressurized fluid conduit 110 to a distal tip 116 thereof. The distal tip 116 of the pressurized fluid conduit 110 can make contact with the occlusion 50 and conduct the thrombolytic wave energy directly to the occlusion 50. This can dislodge the occlusion from the walls of the catheter lumen 22, break up the occlusion 50, or combinations thereof. The occlusion 50 can then be aspirated as described herein.

Advantageously, the pressurized fluid conduit 110, including for example a reinforcement structure 128, can provide an efficient medium for the ultrasonic wave energy to pass through. The pressurized fluid conduit 110 is formed of a relatively stiffer material than the catheter 10 in order to sustain the fluid pressures subjected thereto. This material provides a more efficient media through which ultrasonic energy can pass. By contrast, indwelling catheters are formed of softer materials to facility navigation of tortuous vascular pathways. However, this soft material can absorb wave energy, especially wave energy of high frequencies such as ultrasound, thus attenuating the effects of the ultrasound wave energy on the occlusion.

In an embodiment, the ultrasound transducer 180 introduces ultrasonic wave energy directly to the pressurized fluid passing through the conduit lumen 122. The wave energy can include longitudinal waves, transverse waves, surface waves, or combinations thereof. The wave energy travels through the pressurized fluid to a distal tip 116. The jet of pressurized fluid impinging the occlusion 50 can also conduct the thrombolytic wave energy directly to the occlusion 50. This can dislodge the occlusion from the walls of the catheter lumen 22, break up the occlusion 50, or combinations thereof. The occlusion 50 can then be aspirated as described herein.

Figure 8:
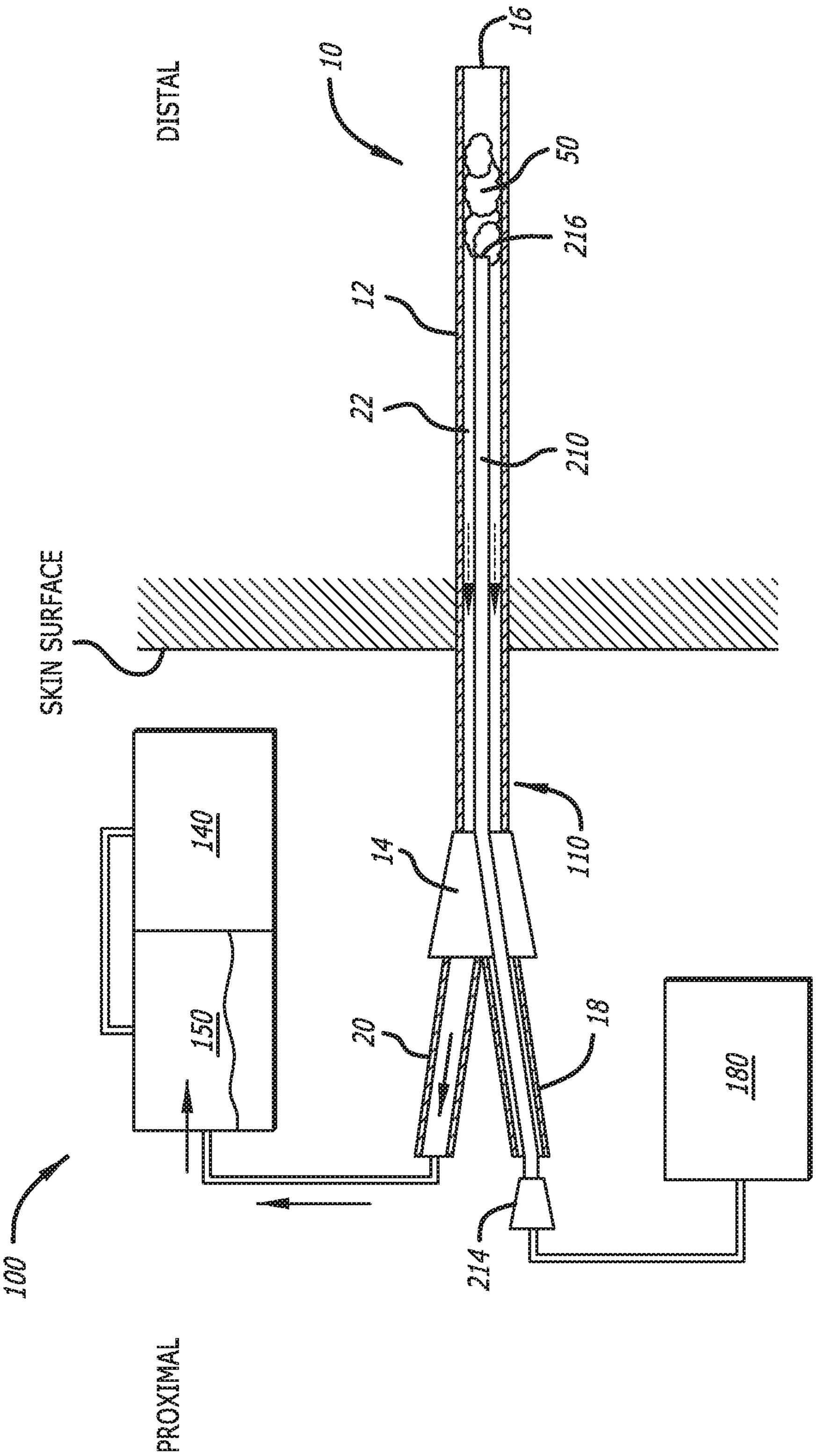
FIG. 8 illustrates an embolectomy system for restoring patency to an implanted catheter, in accordance with embodiments disclosed herein.

As shown in FIG. 8, the embolectomy system 100 includes a stylet 210 that can be introduced to the lumen 22 of the catheter 10 in a similar manner to that of the pressurized fluid conduit 110, as described herein. A distal tip 216 of the stylet 210 can be advanced through the catheter lumen 22 to the occlusion 50. The distal tip 216 can fragment the occlusion 50, which can then be aspirated, as described herein.

In an embodiment, an ultrasound transducer 180 can be coupled with the stylet 210, stylet hub 214, or combinations thereof. The transducer 180 can introduce ultrasonic wave energy, through the stylet 210 to the occlusion 50 to provide thrombolytic energy directly to the occlusion 50, as described herein. This can dislodge the occlusion from the walls of the catheter lumen 22, break up the occlusion 50, or combinations thereof. The occlusion 50 can then be aspirated as described herein.

In an embodiment, the tip 216 of the stylet 210 can include various occlusion removal structures that can further pierce, ablate, grasp, or break up the occlusion 50. Such occlusion removal structures can include sharpened points, helical structures, corkscrew structures, hooks, barbs, pincer arms, sharpened blades, rotating structures, or the like.

In an embodiment, the tip 216 of the stylet 210 can include a stent retrieval structure configured for engaging and grasping the occlusion 50. The stent retrieval structure can grasp and withdraw the occlusion 50 proximally to remove, or break up the occlusion 50. The negative pressure source 140 can concurrently aspirate the occlusion 50, as described herein.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An embolectomy system for restoring patency to an intravascular indwelling catheter having an occlusion disposed therein, the intravascular indwelling catheter including a catheter lumen extending from a proximal end of the intravascular indwelling catheter to a distal end of the intravascular indwelling catheter, the embolectomy system comprising:

a pressurized fluid conduit including a conduit body and a conduit lumen, the conduit body having an outer diameter less than an inner diameter of the catheter lumen to enable insertion and disposition of the pressurized fluid conduit in the catheter lumen, a distal tip of the catheter lumen disposed intravascularly, the conduit body including a nozzle disposed at a distal-most end thereof, the nozzle defining a nozzle lumen having a converging portion disposed proximally and a diverging portion disposed distally;

a positive pressure source in fluid communication with a proximal end of the conduit lumen, the positive pressure source providing a pressurized fluid, the conduit lumen directing the pressurized fluid into the occlusion in the catheter lumen;

a negative pressure source in fluid communication with a proximal end of the catheter lumen disposed external to a vasculature, to aspirate the occlusion from the catheter lumen over at least a portion of an outer surface of the conduit body;

an electrode coupled with a distal tip of the pressurized fluid conduit and configured for detecting one or more ECG signals;

a tip tracking system configured to receive a first ECG signal and a second ECG signal from the electrode and to determine, based on differences in overall amplitude between the first ECG signal and the second ECG signal, if the distal tip of the pressurized fluid conduit is proximate the distal tip of the catheter lumen; and a tip location system for tracking a magnetic element included with a distal portion of the pressurized fluid conduit.

2. The embolectomy system according to claim 1, wherein the pressurized fluid exits the nozzle at an angle relative to a longitudinal axis of the conduit lumen.

3. The embolectomy system according to claim 1, wherein the converging portion extends from a first diameter at a proximal end thereof to a second diameter at a distal end thereof, the second diameter being less than the first diameter, and the diverging portion extends from the second diameter at a proximal end thereof to the first diameter at a distal end thereof.

4. The embolectomy system according to claim 1, wherein the pressurized fluid includes one of water or saline.

5. The embolectomy system according to claim 1, wherein the positive pressure source provides the pressurized fluid of between 0.1 psi to 400 psi.

6. The embolectomy system according to claim 1, wherein the positive pressure source provides the pressurized fluid of between 110 psi to 130 psi.

7. The embolectomy system according to claim 1, wherein the positive pressure source provides a pulsed pressurized fluid that varies in pressure between 0.1 psi and 400 psi at a rate of between 1 Hz to 150 Hz.

8. The embolectomy system according to claim 1, wherein the negative pressure source provides a medical vacuum of between −11 psi and −3 psi.

9. The embolectomy system according to claim 1, wherein the pressurized fluid conduit includes a reinforcement member extending through a portion of a wall of the pressurized fluid conduit.

10. The embolectomy system according to claim 9, wherein the reinforcement member includes a nitinol coil.

11. The embolectomy system according to claim 1, further including an ultrasound transducer coupled to the pressurized fluid conduit or the pressurized fluid and providing ultrasonic wave energy therethrough to the occlusion to fragment the occlusion.

12. The embolectomy system according to claim 1, further including an ultrasound transducer coupled to the intravascular indwelling catheter and providing ultrasonic wave energy through the intravascular indwelling catheter to the occlusion to fragment the occlusion.

13. The embolectomy system according to claim 1, further including a first electrode and a second electrode included with the distal portion of the pressurized fluid conduit, the first electrode configured for detecting an intra-luminal conductance at a first position and the second electrode configured for detecting an intra-luminal conductance at a second position, and a lumen localization system for measuring changes in relative conductance between the first position and the second position to determine a change in intraluminal cross-sectional area, indicating the distal tip of the pressurized fluid conduit is proximate a distal tip of the intravascular indwelling catheter.

14. An embolectomy system for removing an occlusion from an indwelling catheter disposed intravascularly, comprising:

a pressurized fluid conduit including a conduit lumen, a distal tip of the pressurized fluid conduit disposed within a lumen of the indwelling catheter, a distal tip of the indwelling catheter disposed intravascularly;

a positive pressure source in fluid communication with the conduit lumen, the positive pressure source providing a pressurized fluid for ablating the occlusion, the conduit lumen including a nozzle defining a nozzle lumen and disposed at a distal-most end thereof, the nozzle lumen having a converging portion disposed proximally and a diverging portion disposed distally;

a negative pressure source in fluid communication with a proximal end of the lumen of the indwelling catheter and disposed external to a vasculature, the negative pressure source providing a negative pressure for aspirating the occlusion from the indwelling catheter;

an electrode included with the distal tip of the pressurized fluid conduit and configured for detecting one or more ECG signals;

a tip tracking system configured to receive a first ECG signal and a second ECG signal from the electrode and to determine based on differences between the first ECG signal and the second ECG signal if the distal tip of the pressurized fluid conduit is proximate the distal tip of the indwelling catheter; and a tip location system for tracking a magnetic element included with a distal portion of the pressurized fluid conduit.

15. The embolectomy system according to claim 14, wherein the nozzle directs the pressurized fluid at an angle relative to a longitudinal axis of the conduit lumen.

16. The embolectomy system according to claim 14, wherein the converging portion of the nozzle lumen extends from a first diameter at a proximal end thereof to a second diameter at a distal end thereof, the second diameter being less than the first diameter, and the diverging portion of the nozzle lumen extends from the second diameter at a proximal end thereof to the first diameter at a distal end thereof.

17. The embolectomy system according to claim 14, wherein the positive pressure source provides a pulsed pressurized fluid that varies in positive pressure between 0.1 psi and 400 psi at a rate of between 1 Hz to 150 Hz.

18. The embolectomy system according to claim 14, wherein the pressurized fluid conduit includes a reinforcement member.

19. The embolectomy system according to claim 18, wherein the reinforcement member includes a nitinol coil.

20. The embolectomy system according to claim 14, further including a first electrode and a second electrode included with the distal portion of the pressurized fluid conduit, the first electrode configured for detecting an intra-luminal conductance at a first position and the second electrode configured for detecting the intra-luminal conductance at a second position, and a lumen localization system for measuring changes in relative conductance between the first position and the second position to determine a change in intraluminal cross-sectional area, indicating the distal tip of the pressurized fluid conduit is proximate the distal tip of the indwelling catheter.

21. The embolectomy system according to claim 14, further including an ultrasound transducer coupled to one of the pressurized fluid conduit, the indwelling catheter, or the pressurized fluid and configured to provide ultrasonic wave energy therethrough to the occlusion to fragment the occlusion.

* * * * *